(12) United States Patent
McCoy et al.

(10) Patent No.: US 6,531,112 B2
(45) Date of Patent: Mar. 11, 2003

(54) FORMULATIONS FOR ADMINISTERING CALCITONIN AND PROCESSES FOR PREPARING THE SAME

(75) Inventors: Randall E. McCoy, Little Falls, NJ (US); Robert O. Williams, III, Austin, TX (US); Miles A. Libbey, III, Pennington, NJ (US)

(73) Assignee: DelRx Pharmaceutical Corporation, Jamesburg, NJ (US)

( * ) Notice: Subject to any disclaimer, the term of this patent is extended or adjusted under 35 U.S.C. 154(b) by 0 days.

(21) Appl. No.: 09/855,175

(22) Filed: May 14, 2001

(65) Prior Publication Data
US 2002/0132757 A1 Sep. 19, 2002

Related U.S. Application Data
(60) Provisional application No. 60/204,308, filed on May 15, 2000.

(51) Int. Cl.[7] .............................. A61K 9/12; A61K 9/14
(52) U.S. Cl. .......................... 424/46; 424/45; 424/434; 424/435; 424/489; 514/4; 514/9; 128/200.14
(58) Field of Search ........................ 424/45, 46, 434, 424/435, 489; 514/9, 4; 128/200.14

(56) References Cited

U.S. PATENT DOCUMENTS

| 5,011,678 A | * | 4/1991 | Wang et al. .................. 424/45 |
| 5,719,122 A | * | 2/1998 | Chiodini et al. ............... 514/9 |
| 5,759,565 A | * | 6/1998 | Azria et al. .................. 424/434 |

FOREIGN PATENT DOCUMENTS

JP            173074     * 11/1995

* cited by examiner

*Primary Examiner*—Jose' G. Dees
*Assistant Examiner*—M. Haghighatian
(74) *Attorney, Agent, or Firm*—Mathews, Collins, Shepherd & McKay, P.A.

(57) ABSTRACT

The present invention provides a non-invasive method for administering polypeptides across epithelial membranes. The formulations in the present invention comprise solid polypeptide particles mixed with a permeation enhancer and excipients which are dispersed in a media for oral or intranasal administration. Also provided in the present invention is a process to prepare the formulations.

17 Claims, No Drawings

FORMULATIONS FOR ADMINISTERING CALCITONIN AND PROCESSES FOR PREPARING THE SAME

REFERENCE TO PREVIOUS APPLICATIONS

This application claims benefit of U.S. Provisional Application No. 60/204,308 filed on May 15, 2000 entitled "Formulations for Administering Calcitonin and Process for Preparing the Same", hereby incorporated by reference into this application.

1. Field of the Invention

The present invention relates to formulations for non-invasive delivery of calcitonin across mucous membranes by oral or inhalant routes to patients and to processes for preparing the formulations.

2. Description of the Prior Art

Effective, convenient, and comfortable delivery of calcitonin to patients is an area of major concern. A conventional mode of delivery for many drugs is by oral ingestion of pills or tablets that disintegrate into primary particles, and release the drug for absorption into the patient's bloodstream from the stomach and gastrointestinal (GI) tract. However, calcitonin is not suitable for conventional modes of delivery such as oral delivery, as it is susceptible to enzymatic degradation, and its large size and hydrophilic nature makes it ill suited for absorption through the GI tract. Saliva and/or gastrointestinal compounds tend to degrade or digest the calcitonin, rendering it ineffective.

Efforts have recently been made to develop more effective routes for administering calcitonin. See, e.g., U.S. Pat. No. 5,726,154, "Stabilization and Oral Delivery of Calcitonin"; U.S. Pat. No. 5,441,933, "Pharmaceutical Compositions and Dosage Forms for the Oral Delivery of Calcitonin"; and U.S. Pat. No. 5,281,580, "Calcitonin-containing Emulsion for Nasal Administration," each of which is incorporated herein. However, issues such as compositional stability, patient convenience, and difficulty in fabrication (e.g., cost) often need to be considered as the formulations and delivery methods are developed. There remains a need for a relatively simple process and formulation for conveniently and effectively administering calcitonin, particularly methods that are applicable for oral mucosal administration and provide a more efficient and reliable bioavailability.

DESCRIPTION OF THE INVENTION

This invention provides a formulation useful for conveniently delivering calcitonin to a targeted area. One aspect of the present invention is a stabilized form of calcitonin resistant to chemical and enzymatic degradation. The solid particles are less exposed to potential deleterious components of the formulation. In another aspect of the invention, a formulation is provided that is adapted for oral (buccal) delivery of calcitonin. In this formulation, an effective amount of calcitonin is mixed with an "oral absorption enhancer" in a carrier solvent, preferably also in the presence of a surfactant. The oral cavity presents a large exposed mucous membrane through which the calcitonin can be absorbed. Incorporating the permeation enhancer into the particle or onto the surface of the solid particles increases the effective concentration of the permeation enhancer at the uptake site. This reduces the concentration required in the bulk solvent which decreases the likelihood of nonspecific irritation. Thus the formulation is optimized for oral absorption directly through the buccal mucosa of the oral cavity. The carrier solvent preferably is non-aqueous which further limits the exposure of the solid calictonin particles to hydrolytic degradation.

For example, an exemplary formulation adapted for oral mucosal delivery according to this aspect of the invention includes at least three components: (1) an effective amount of calcitonin; (2) an oral absorption enhancer for disrupting or modifying the absorptive surface of the targeted site (such as wetting) to improve absorption across the membrane; (3) an optional formulation surfactant for increasing the miscibility of the formulation ingredients or reducing the size of the calcitonin to droplet size suitable for intra-oral delivery (e.g., 5–200 $\mu$m); and (4) a carrier solvent.

The term "alkyl group" as used herein means a saturated, monovalent, unbranched or branched hydrocarbon chain. Examples of alkyl groups include, but are not limited to, $C_6$—$C_{20}$ alkyl groups, such as hexyl, heptyl, and octyl, decyl, dodecyl tetradecyl, hexadecyl, octadecyl. An alkyl group can be unsubstituted or substituted/with one or two suitable substituents.

The term "alkenyl group" as used herein means a monovalent, unbranched or branched hydrocarbon chain having one or more double bonds therein. The double bond of an alkenyl group can be unconjugated or conjugated to another unsaturated group. The double bond can be E or Z isomers. Suitable alkenyl groups include, but are not limited to $C_6$—$C_{20}$ alkenyl groups, such as hexenyl, hexadienyl, (Z)-octadec-12-enyl, (E)-octadec-12-enyl, (Z)-tetradec-10-enyl. An alkenyl group can be unsubstituted or substituted with one or two suitable substituents.

Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. Preferred oral absorption enhancers for the present invention include sulfates, $RSO_4^-M^+$, wherein R is selected from a group consisting of $C_6$—$C_{20}$ alkyl and $C_6$—$C_{20}$ alkenyl and M is an alkali metal cation. An especially preferred oral absorption enhancer for the present invention is sodium lauryl sulfate.

The formulation surfactant may be selected from surfactants such as benzalkonium chloride, benzethonium chloride, polysorbate 80, sodium lauryl sulfate, Brij surfactants (e.g., polyoxy(n)-oleoethers, wherein n is from 1 to 100), Tween surfactants (e.g., sorbitan monooleate {Span 80} and sorbitan monolaurate {Span 20}), Pluronic surfactants (e.g., Pluronic F77), lecithin, oleic acid, polyoxyethylene, and dioctyl sodium sulfosuccinate (Aerosol OT).

The carrier solvent preferably is a non-aqueous carrier solvent selected from ethanol, glycerol, propylene glycol, polyethylene glycol, sorbitol, vitamin E and derivatives of vitamin E, and polyvinylpyrrolidone.

According to another aspect of the invention, a formulation adapted for non-invasive transmucosal delivery is comprised of solid phase particles suspended in a delivery medium. With this formulation, dehydrated solid-phase particles are composed of calcitonin containing with at least one of a surfactant and a permeation enhancer, and suspended in a suspension medium such as a pharmaceutically acceptable carrier or propellant system. The suspension medium is preferably a non-aqueous carrier solvent as described above. The formulation may be applied to the buccal cavity by intraoral administration, or by inhalation to the pulmonary or nasal region. The delivery device transports the suspended particles contained in droplets aerosolized from the device, where the surfactant and/or permeation enhancer enable the absorption of the calcitonin through the buccal, pulmonary or nasal epithelial membrane. The permeation enhancers increase membrane permeability and facilitate drug transport through the biological membranes, thereby enhancing the bioavailablity of the delivered calcitonin. Suitable permeation enhancers and surfactants may be selected from the compounds referenced above. The calcitonin is then transported through the buccal epithelial membrane at the area where the peptide was deposited and reaches the systemic blood circulation. With this invention, the formulation may be delivered via an atomized spray or liquid, thereby avoiding the pains and discomfort encountered with invasive modes of delivery by injection.

Applying the inventive concepts described herein, each dose of calcitonin may be separately included within a container, such that single doses of calcitonin can be conveniently administered. Also, the calcitonin may be provided with a delivery system including a container, a metering pump/valve fitted to the container, and an actuator, such that a single dose may be administered by actuating the metering pump/valve fitted to the container. By co-administration of the calcitonin and permeation enhancers to the target region, the permeability of the epithelial membrane can be increased, thereby increasing the bioavailability of the calcitonin. Furthermore, timed-release of the calcitonin may be achieved by applying the dehydrated solid-phase particle size embodiment of the invention. The concentration of surfactant and/or permeation enhancer can be adjusted to modify the timing of the absorption of the calcitonin into the patient's bloodstream.

The formulations of this invention may be delivered via an aerosol spray or drops. A propellant system for a propellant-driven aerosol formulation may consist of one or a combination of the pharmaceutically acceptable propellants, including hydrofluorocarbons (HFA 134a, HFA 227), chlorofluorocarbons (CFC 11, CFC 12, CFC 114), hydrocarbons (propane, butane, isobutane, etc.), and dimethyl ether. HFA 134a and HFA 227 are preferred propellants due to the restriction in production and use of CFC propellants. Ethanol can be incorporated into the formulation as a dispersing aid and a cosolvent for the surfactants, with its level ranging from 0% w/w to 50% w/w. A typical level of ethanol is 5–20% w/w. Other solvents or co-solvents may be used, as referenced above. Preferably, the formulation is non-aqueous. However, if an aqueous-based system is prepared, the product advantageously may be preserved against microbial growth since this may affect the chemical stability of the ingredients, safety, and acceptability of the product, and the physical integrity of the system. Applying the solid particle embodiment of the invention, an inhalation mode of administration is also contemplated. In this case, the formulation can be packaged and used in a similar manner as a pressurized metered-dose inhaler (pMDI). The invention will accurately deliver an aerosolized dose to the pulmonary region of a patient by oral inhalation, or to the nasal cavity of a patient by nasal application. For a topical mode of administration, the formulation (solid-phase based) can be packaged in the form of a metered-dose applicatorTM (MDA) and sprayed directly to the targeted sites of the body, which include, but are not limited to the buccal mucosa, sublingual area and skin.

The invention also comprises an advantageous method of preparing formulations for delivering calcitonin by non-invasive routes as follows. A quantity of calcitonin is dissolved in a pharmaceutically acceptable buffer, such as acetate buffer, lactate buffer, phosphate buffer, or the like, to form a solution with a target pH of 3 to 8. A preferred calcitonin concentration for the solution is 2–30 mg/ml. The solution is mixed with at least one pharmaceutically acceptable surfactant and at least one permeation enhancer (as described above) which can be a surfactant as well. The surfactants and the permeation enhancer are preferably soluble in water, such that a homogeneous solution is formed after the calcitonin solution is mixed with the agents.

The solution containing calcitonin and the surfactant and/or permeation enhancer is subsequently lyophilized (freeze-dried) to form dehydrated, solid-phase particles. The particles can also be prepared by spray drying, evaporation and other techniques well known in the art and the present invention is not limited to any specific technique. The dehydrated solid-phase particles may be further mixed with other pharmaceutical excipients to form the dosage form, including, but not limited to aqueous or propellant based solutions or suspensions for aerosol delivery. The aqueous aerosol formulation can then be delivered as an aerosolized dose with a metering pump system. For example, to prepare a propellant-driven aerosol, the obtained dehydrated solid phase particles (as described above) can be dispersed in ethanol, if desired, to form a homogenous dispersion which then may be transferred to a pressure-resistant container. A metering valve that is suitable for accurate and reproducible delivery of aerosol doses may be fitted and crimped to the container, and one or a combination of liquefied propellants can be filled into the container to form a suspension system containing the dehydrated solid-phase particles composed of calcitonin and functional excipients. The obtained formulation can be used as a pressurized metered-dose inhaler or applicator suitable for aerosol delivery by propellant or metered-valve systems.

The exemplary formulations according to this invention have superior chemical stability after storage at ambient conditions. This constitutes yet another advantage of this invention over conventional dosage forms for calcitonin. The invention will be better understood from the following examples. However, those of ordinary skill in the art will readily understand that these Examples are merely illustrative of the invention.

EXAMPLE 1

| Ingredient | Approx. % w/w |
| --- | --- |
| Calcitonin | 0.5–5 |
| Permeation enhancer(s) | 1.2–10 |
| Carrier-solvent | |
| Ethanol | 8–20 |
| Buffer | 0.01–20 |
| Propellant | q.s. to 100% |

The ingredients (calcitonin, buffer) are thoroughly mixed to form a solution. At least one permeation enhancer is added and dissolved. The solution is lyophilized to remove the water and form dehydrated solid particles containing drug and functional excipients. The suspension is placed within a pressure-resistant can and administered intra-orally to provide calcitonin to a patient in need thereof

EXAMPLE 2

Calcitonin is weighed in a clean glass container and dissolved in a buffer, such as a lactate buffer, at a suitable pH. Brij 98 and sodium lauryl sulfate are added to the calcitonin solution to form a homogenous solution. The mixture is lyophilized and the dehydrated solid particles are suspended in ethanol. The ethanol slurry is added to a pressure-resistant can, a valve is crimped on, and hydrofluoroalkane (HFA-134a) filled through the valve into the canister. The composition of the formulation is presented as follows:

| | Concentration of Each Pharmaceutical Ingredient (Percentage is expressed on w/w basis) |
|---|---|
| Calcitonin | 1.0% |
| Brij 98 | 0.9% to >1.0% |
| Sodium Lauryl Sulfate | 1% |
| Anhydrous Ethanol | 20% |
| HFA 134a | q.s. to 100% |

The formulation is presented as a readily redispersible suspension in which dehydrated solid-phase particles containing calcitonin are suspended in HFA 134a for effective aerosol delivery of calcitonin to a targeted site.

EXAMPLE 3

A formulation is presented as follows:

| | Concentration of Each Pharmaceutical ingredient (Percentage is expressed on w/w basis) |
|---|---|
| Calcitonin | 1.0% |
| Brij 98 | 0.9% |
| Sodium Lauryl Sulfate | 5% |
| sodium salicylate | 1–5% |
| Anhydrous Ethanol | 20% |
| HFA 134a | q.s. to 100% |

EXAMPLE 4

A formulation is presented as follows:

| | Concentration of Each Pharmaceutical Ingredient (Percentage is expressed on w/w basis) |
|---|---|
| Calcitonin | 1.0% |
| Pleuronic | 0.9% |
| Sodium Lauryl Sulfate | 1% |
| Anhydrous Ethanol | 20% |
| HFA 134a | q.s. to 100% |

EXAMPLE 5

A process for obtaining a formulation according to the invention is as follows. A suitable amount of calcitonin is weighted in a clean glass container and dissolved in citrate buffer at a suitable pH. NaCl, Tween 80 and sodium lauryl sulfate are added in selected ratios to the calcitonin solution to form a homogenous solution. The mixture is lyophilized and the dried particles are suspended in hydrofluoroalkane (HFA) 134a in the presence of ethanol (e.g., at 8–20% of the formulation). The formulation is contained in a pressure-resistant container which is fitted with a metering valve. A composition for effective aerosol delivery of calcitonin is presented.

We claim:

1. A formulation for the transmucosal delivery of calcitonin to a patient comprising:
   i) a suspension of dehydrated solid particles in a delivery medium wherein said solid particles comprise a dehydration product of calcitonin and at least one orally effective membrane permeation enhancer selected from the group consisting of a sodium alkyl sulfate, a sodium alkenyl sulfate and sodium salicylate; and,
   ii) the delivery medium comprising a fluid, the dehydrated solid particles being suspended in an orally-acceptable solvent or carrier, and adapted for spray delivery of the dehydrated solid particles to the buccal mucosa.

2. A formulation according to claim 1 wherein said dehydrated solid particles are lyophilized and essentially dehydrated calcitonin particles.

3. A formulation according to claim 1 further comprising a pharmaceutically acceptable surfactant deposited on said dehydrated solid particles for increasing the miscibility of the ingredients or reducing the droplet size.

4. A formulation according to claim 1 wherein said membrane permeation enhancer is $RSO_4^-M^+$ wherein;
   a. R is selected from a group consisting of $C_6$–$C_{20}$ alkyl and $C_6$–$C_{20}$ alkenyl; and,
   b. M is an alkali metal cation.

5. A formulation according to claim 3 wherein said surfactant is a nonionic surfactant.

6. A formulation according to claim 1 wherein said solvent or carrier is selected from a group consisting of ethanol, glycerol, glycol, propylene glycol, polyethylene glycol, sorbitol, Vitamin E, derivatives of Vitamin E and polyvinylpyrrolidone.

7. A formulation according to claim 1 wherein said membrane permeation enhancer is sodium lauryl sulfate, said surfactant is a polyoxyethylene ether surfactant and said solvent is ethanol.

8. A formulation according to Claim 1 wherein said membrane permeation enhancer is at least one of sodium lauryl sulfate or sodium salicylate, said surfactant is a polyoxyethylene and polyoxypropylene block copolymer surfactant and said solvent is ethanol.

9. A formulation according to claim 1 wherein said membrane permeation enhancer is at least one of sodium lauryl sulfate or sodium salicylate said surfactant is a polyoxyethylene sorbitan monolaurate, polyoxyethylene sorbitan monooleate, surfactant and said solvent is ethanol.

10. A formulation according to claim 1 which further comprises a propellant.

11. A formulation according to claim 10 wherein the propellant is HFA 134a or HFA 227.

12. A formulation for the non-invasive delivery of calcitonin comprising,
   i) substantially aqueous free particles of calcitonin mixed with at least one of a permeation enhancer selected from the group consisting of a sodium alkyl sulfate, a sodium alkenyl sulfate and sodium salicylate and a surfactant; and, ii) a delivery medium comprising at least one of a suspending media or a pharmaceutically-acceptable propellant;

the substantially aqueous fee particles being suspended within the delivery medium to define the formulation adapted for non-invasive delivery to the patient's targeted site where the permeation enhancer modifies the buccal mucosa to initiate or enhance absorption of said calcitonin.

13. A process for preparing a formulation for use in delivering calcitonin to the buccal mucosa of a patient, the process comprising the steps of:

i) obtaining a quantity of said calcitonin;

ii) dissolving said calcitonin in a pharmaceutically acceptable buffer to form a solution with a pH from about 3 to about 8;

iii) mixing said solution with at least one pharmaceutically acceptable surfactant and at least one orally effective membrane permeation enhancer selected from the group consisting of a sodium alkyl sulfate, a sodium alkenyl sulfate and sodium salicylate to form a homogenous solution; and, iv) lyophilizing the homogeneous solution to form dehydrated solid particles comprising calcitonin mixed with said surfactant and said permeation enhancer.

14. The process of claim 13, further comprising the step of dispersing said dehydrated solid particles containing calcitonin in suspending media or a pharmaceutically acceptable propellant.

15. A process according to claim 13 wherein the buffer is a citrate buffer, the absorption enhancer is sodium lauryl sulfate, the surfactant is Tween 80, and the propellant is HFA 134a.

16. A process according to claim 13 wherein the buffer is a citrate buffer, the absorption enhancer is sodium lauryl sulfate, the surfactant is polyethylene glycol sorbitan monooleate, and the suspending media is ethanol.

17. A formulation according to claim 1 wherein said calcitonin particles were produced by lyophilization of a buffered aqueous calcitonin solution.

* * * * *